United States Patent [19]

Fennhoff

[11] Patent Number: 5,914,431
[45] Date of Patent: Jun. 22, 1999

[54] COCATALYSTS FOR THE SYNTHESIS OF BISPHENOLS

[75] Inventor: Gerhard Fennhoff, Antwerp, Belgium

[73] Assignee: Bayer AG, Germany

[21] Appl. No.: 08/932,148

[22] Filed: Sep. 17, 1997

[30] Foreign Application Priority Data

Sep. 23, 1996 [DE] Germany .............................. 196 38 888

[51] Int. Cl.⁶ .................................................... C07C 39/12
[52] U.S. Cl. ............................................ 568/719; 548/487
[58] Field of Search ..................... 568/722, 723, 568/727, 719; 548/487

[56] References Cited

U.S. PATENT DOCUMENTS

| | | |
|---|---|---|
| 2,191,831 | 2/1940 | Perkins . |
| 2,468,982 | 5/1949 | Jansen . |
| 2,623,908 | 12/1952 | Stoesser et al. . |
| 2,775,620 | 12/1956 | Williamson . |
| 3,182,308 | 5/1965 | Dutton et al. . |
| 4,912,263 | 3/1990 | Rudolph et al. . |
| 5,212,206 | 5/1993 | Rudolph et al. . |
| 5,284,981 | 2/1994 | Rudolph et al. . |
| 5,589,517 | 12/1996 | Sugawara et al. . |

FOREIGN PATENT DOCUMENTS

| | | |
|---|---|---|
| 3619450 | 12/1987 | Germany . |
| 3727641 | 3/1989 | Germany . |
| 19518406 | 11/1996 | Germany . |
| 06228035 | 8/1994 | Japan . |

OTHER PUBLICATIONS

Chemical Abstracts, vol. 58, p. 1403e.

Ullmanns Encyclopäedie der Techischen Chemie, Fourth Edition, Verlag Chemie, vol. 18, *Phenol–Derivate*, pp. 191–214 (1979).

Ullmanns Encyclopäedie der Techischen Chemie, Fourth Edition, Verlag Chemie, vol. 9, *Chlorophenole*, pp. 573–582 (1975).

Ullmanns Encyclopäedie der Techischen Chemie, Fourth newly revised and enlarged edition, Verlag Chemie, Weinheim, New York, vol. 15, *Kresole and Xylenole*, pp. 61–77 (1978).

*Primary Examiner*—Michael L. Shippen
*Attorney, Agent, or Firm*—Connolly & Hutz

[57] ABSTRACT

The invention relates to the synthesis of bisphenols from monophenols and carbonyl compounds such as aldehydes and ketones using concentrated mineral acids such as hydrochloric acid and/or hydrogen chloride gas as acid catalysts and a mercaptan as cocatalyst, which is fixed by an ion pair bond to a matrix that is insoluble in the reaction medium.

24 Claims, No Drawings

COCATALYSTS FOR THE SYNTHESIS OF BISPHENOLS

BACKGROUND OF THE INVENTION

1. Field of the Invention

The invention relates to the synthesis of bisphenols from monophenols and carbonyl compounds such as aldehydes and ketones using concentrated mineral acids such as hydrochloric acid and/or hydrogen chloride gas as acid catalysts and a mercaptan as cocatalyst, which is fixed by an ion pair bond to a matrix that is insoluble in the reaction medium.

2. Description of the Prior Art

The condensation of phenols and carbonyl compounds to form bisphenols with the use of catalysts such as hydrochloric acid (U.S. Pat. Nos. 3,182,308; 2,191,831) and of sulphur-containing compounds as cocatalysts is known (for example, from U.S. Pat. Nos. 2,468,982; 2,623,908, the use of thioglycolic acid and 3-mercaptopropionic acid; from U.S. Pat. No. 2,775,620, the addition of alkyl mercaptans; from Chemical Abstracts 58, 1403e, the addition of hydrogen sulphide). The known sulphur-containing cocatalysts can in practical operation lead to considerable discolorations of the bisphenols and of subsequent products prepared from them such as, for example, polycarbonates, copolycarbonates, polyesters, copolyesters and epoxy resins, if they are not separated so as to leave no residue by means of appropriate purification steps such as, for example, crystallisation of the bisphenol and washing out of the sulphur compounds. Particularly in the case of bisphenols for which the syntheses require very high concentrations of cocatalysts, the separation of the sulphur-containing components is frequently difficult and is associated with undesirable losses of the required target compound, particularly where there is heat stress, for example, during the working-up process.

In contrast, cocatalysts can easily be completely separated by filtration or centrifugation if they are not added in homogeneous phase but, before addition to the educt mixture, are already bonded by ionic bonds to a matrix which is insoluble in the reaction medium. This form of cocatalyst permits extremely high cocatalyst concentrations to be used without the occurrence of the problems regarding quality described above.

The synthesis of bisphenols using cocatalysts fixed to a resin matrix is described in DE-A 3 619 450 (for example, using aminoalkyl mercaptan units) or in DE-A 3 727 641 (for example, using thiazolidine units); the acid catalyst likewise needed here is also bonded in the form of sulphonic esters to the resin matrix.

SUMMARY OF THE INVENTION

It has now been found that bisphenols corresponding to formula (I) can be prepared without difficulty using concentrated mineral acids such as hydrochloric acid and/or hydrogen chloride gas together with a sulphonic acid ion-exchange resin based on a cross-linked polystyrene resin matrix, the sulpho groups of which have been partly, preferably completely, neutralised with an aminomercaptan and/ or a thiazolidine, with high conversions of ketone and very high selectivities of 90% to 100%, complete conversion of the ketone being attained after shorter reaction times than is the case where the corresponding cocatalysts such as mercaptans are used in the homogeneous phase.

The present invention therefore provides a process for the preparation of bisphenols corresponding to formula (I)

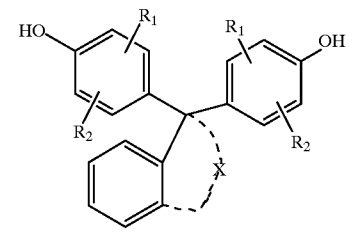

by reaction of phenols corresponding to the formula

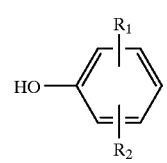

with ketones corresponding to the formula

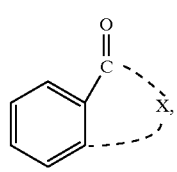

wherein $R_1$ and $R_2$ independently of one another denote hydrogen, halogen, preferably chlorine or bromine, $C_1$–$C_8$ alkyl, $C_5$–$C_6$ cycloalkyl, $C_6$–$C_{10}$ aryl, preferably phenyl and $C_7$–$C_{12}$ aralkyl, preferably phenyl-$C_1$–$C_4$-alkyl, in particular benzyl and X represents

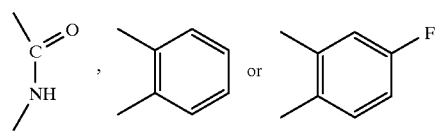

DESCRIPTION OF THE PREFERRED EMBODIMENTS

The phenols corresponding to formula (II) are either known in the literature or are obtainable by methods known in the literature (see, for example, for cresols and xylenols: Ullmanns Encyclopädie der technischen Chemie, Fourth newly revised and enlarged edition, Volume 15, pages 61 to 77, Verlag Chemie, Weinheim, N.Y., 1978; for chlorophenols: Ullmanns Encyclopädie der technischen Chemie, Fourth edition, Verlag Chemie, 1975, Volume 9, pages 573 to 582; and for alkylphenols: Ullmanns Encyclopädie der technischen Chemie, Fourth edition, Verlag Chemie, 1979, Volume 18, pages 191 to 214).

Examples of suitable phenols corresponding to formula (II) are:

phenol, o-cresol, m-cresol, 2,6-dimethylphenol, 2-chlorophenol, 3-chlorophenol, 2,6-dichlorophenol, 2-cyclohexylphenol, diphenylphenol and o- and p-benzylphenols.

Examples of the ketones (III) are:

isatin, 9-fluorenone and 2-fluoro-9-fluorenone

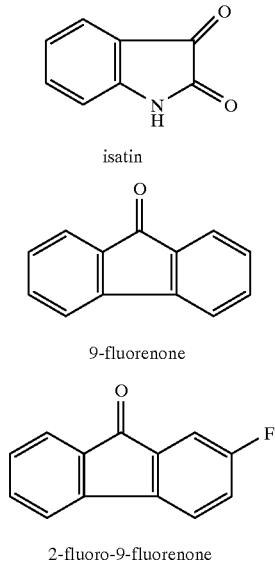

isatin 9-fluorenone 2-fluoro-9-fluorenone

The process is characterised in that a mineral acid, preferably hydrochloric acid and/or hydrogen chloride gas, is added as catalyst to a mixture of a phenol (II), a ketone (III) and a sulphonic acid ion-exchange resin based on a cross-linked polystyrene resin matrix, the sulpho groups of which have been neutralised, to the extent of at least 10% and preferably completely, by means of a mercaptoamine and/or a thiazolidine, the reaction temperatures being maintained at between 20° C. and 90° C., preferably between 25° C. and 40° C. The subsequent separation of the acidic ion-exchange resin is carried out by filtration at 65° C. to 90° C., after the hydrochloric acid and/or hydrogen chloride gas has been separated off, which preferably takes place by lowering the pressure at temperatures of between 30° C. and 70° C. The product is then purified according to the conventional methods by recrystallisation in phenol, phenol and water or in other suitable organic solvents.

The mineral acid used is preferably a mixture of 36% hydrochloric acid and hydrogen chloride gas. 1 kg of 36% hydrochloric acid and 1 kg of hydrogen chloride gas are used per 18 to 180 mol of a ketone (III). Hydrogen chloride gas is particularly preferably used without hydrochloric acid, the concentration of the hydrogen chloride gas in the reaction mixture in this case being between 0.5 wt. % and 5 wt. %, preferably between 1.0 wt. % and 2.0 wt. %, based on the total reaction mixture inclusive of the hydrogen chloride gas.

The cocatalyst used is a sulphonic acid ion-exchange resin based on a cross-linked polystyrene, the acidic groups of the ion-exchange resin having been neutralised, to the extent of at least 10% but preferably completely, by mercaptoamines and/or thiazolidines before its use in the reaction mixture and the quantity of the cocatalyst used according to the invention being selected so that the molar ratio of mercapto groups to ketone is at least 1:10, preferably 1:1 to 10:1.

Before its use in the bisphenol synthesis, the acidic ion-exchange resin is washed with distilled or deionised water until the washings exhibit a conductivity of <100 μS. The water is then removed from the ion-exchange resin by drying in conventional drying units or by displacement with anhydrous phenol. Finally, the ion-exchange resin is partly or completely neutralised in phenolic suspension by means of a mercaptoamine and/or a thiazolidine.

The degree of cross-linking of these polystyrenes may be between 0.5% and 50%, preferably between 1% and 8%. Here the degree of cross-linking means the quantity of cross-linking comonomer used in mol-%. based on the mols of styrenes used during the copolymerisation.

The mercaptans used are preferably ω-aminoalkyl mercaptans and the preferred thiazolidine is 2,2-dimethylthiazolidine.

The bisphenols prepared according to the present invention are particularly suitable for the synthesis of polycarbonates, copolycarbonates, polyesters, copolyesters and epoxy resins.

EXAMPLES

A. Preparation of the Ion-Exchange Resin as Cocatalyst for the Bisphenol Synthesis 300 g of water-moistened, acidic ion-exchange resin (Lewatit SC 102, Bayer AG) is washed with demineralised water until the washings exhibit a conductivity of <100 μS. The Lewatit SC 102 is then filtered off with strong suction over a vacuum nutsch and dried in a vacuum drying cabinet for 72 hours at 100° C. and 20 mbar. The weighed sample after drying yields approximately 60 g of dry Lewatit SC 102.

60 g of dry ion-exchange resin Lewatit SC 102 is stirred for 4 hours in 300 ml of phenol (water content <0.1%), in order that it may swell completely. 26.5 g of 2,2-dimethylthiazolidine in 100 ml of phenol is then added and the mixture is stirred in a round-bottom flask at 65° C. for 24 hours. The resin is then removed by filtration, filtered under strong suction and the bisphenol A formed and the unbonded dimethylthiazolidine are eluted with fresh phenol until bisphenol A and dimethylthiazolidine can no longer be detected in the eluate.

B. Synthesis of the Bisphenols

Example 1

Hydrogen chloride gas is introduced over a period of 1 hour into a mixture comprising 499 g of phenol, 37 g of 9-fluorenone, 3.74 g of 36% hydrochloric acid and 125 g of the ion-exchange resin prepared in A, contained in a stirred vessel at 30° C. Stirring is continued for 5 hours, after which the ketone conversion and the selectivity of the reaction are determined.

Ketone conversion: 95–100%

Selectivity: 94–96%

Example 2

The procedure is as in Example 1, but 41 g of 2-fluoro-9-fluorenone is used instead of 9-fluorenone.

Ketone conversion: 95–100%

Selectivity: 94–96%

Example 3

The procedure is as in Example 1, but 30 g of isatin is used instead of 9-fluorenone.

Ketone conversion: 98–100%

Selectivity: 90–96%

Example 4

Hydrogen chloride gas is introduced over a period of 1 hour into a mixture comprising 499 g of phenol, 37 g of 9-fluorenone and 125 g of the ion-exchange resin prepared in A, contained in a stirred vessel at 30° C. Stirring is continued for 5 hours, after which the ketone conversion and the selectivity of the reaction are determined.

Ketone conversion: 98–100%

Selectivity: 95–98%

Example 5

The procedure is as in Example 4, but 41 g of 2-fluoro-9-fluorenone is used instead of 9-fluorenone.

Ketone conversion: 95–100%

Selectivity: 94–98%

Example 6

The procedure is as in Example 4, but 30 g of isatin is used instead of 9-fluorenone.

Ketone conversion: 97–100%

Selectivity: 95–98%

What is claimed is:

1. A process for preparing bisphenols corresponding to the formula:

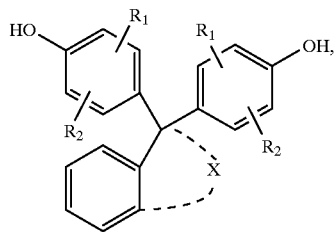

(I)

the process comprising reacting phenols corresponding to the formula:

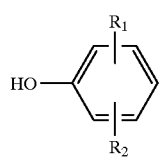

(II)

with ketones corresponding to the formula:

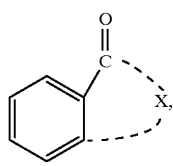

(III)

wherein

R$_1$ and R$_2$, independently of one another, denote hydrogen, halogen, C$_1$–C$_8$ alkyl, C$_5$–C$_6$ cycloalkyl, C$_6$–C$_{10}$ aryl or C$_7$–C$_{12}$ aralkyl, and X represents

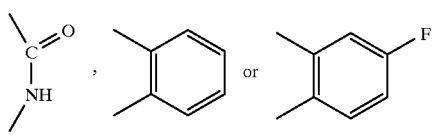

in the presence of a catalyst and a cocatalyst, the catalyst comprising a mineral acid, and the cocatalyst comprising a sulphonic acid ion-exchange resin based on a cross-linked polystyrene, wherein the ion-exchange resin includes acidic groups having been previously neutralized to an extent of at least 10% by weight by mercaptoamines, thiazolidines, or a mixture thereof.

2. The process according to claim 1, wherein the ion-exchange resin is prepared before its use by washing it with distilled or deionised water until the washings exhibit a conductivity of <100 $\mu$S, then removing the water from the ion-exchange resin by drying it in a drying unit or by displacing it with anhydrous phenol, and thereafter partly or completely neutralising it with the mercaptoamines, the thiazolidines, or the mixture thereof.

3. The process according to claim 1, further comprising removing the mineral acid and separating the ion-exchange resin from the bisphenols.

4. The process according to claim 3, wherein the separating step is carried out by filtering or centrifugating the ion-exchange resin from the bisphenols.

5. The process according to claim 3, further comprising purifying the bisphenols.

6. The process according to claim 1, wherein the mineral acid is hydrochloric acid, hydrogen chloride gas, or a mixture thereof.

7. The process according to claim 1, wherein the phenols are selected from the group consisting of phenol, o-cresol, m-cresol, 2,6-dimethylphenol, 2-chlorophenol, 3-chlorophenol, 2,6-dichlorophenol, 2-cyclohexylphenol, diphenylphenol, o-benzylphenol, and p-benzylphenol.

8. The process according to claim 1, wherein the ketones are selected from the group consisting of isatin, 9-fluorenone, and 2-fluoro-9-fluorenone.

9. The process according to claim 1, wherein the mercaptoamines comprise ω-aminoalkyl mercaptans.

10. The process according to claim 1, wherein the thiazolidines comprise 2,2-dimethylthiazolidine.

11. The process according to claim 1, wherein the acidic groups of the ion-exchange resin are neutralised by the mercaptoamines or the mixture of mercaptoamines and thiazolidines, and in which a molar ratio of mercapto groups to ketones is at least 1:10.

12. The process according to claim 11, wherein the molar ratio of mercapto groups to ketones is between about 1:1 and 10:1.

13. A process for preparing a bisphenol corresponding to the formula:

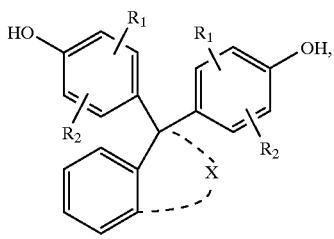
(I)

the process comprising reacting a phenol corresponding to the formula:

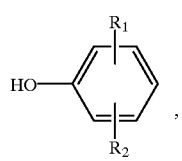
(II)

with a ketone corresponding to the formula:

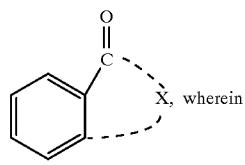
(III)

$R_1$ and $R_2$, independently of one another, denote hydrogen, halogen, $C_1-C_8$ alkyl, $C_5-C_6$ cycloalkyl, $C_6-C_{10}$ aryl or $C_7-C_{12}$ aralkyl, and
X represents:

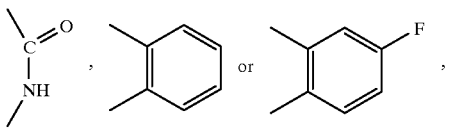

in the presence of a catalyst and a cocatalyst, the catalyst comprising a mineral acid, and the cocatalyst comprising a sulphonic acid ion-exchange resin based on a cross-linked polystyrene, wherein the ion-exchange resin includes an acidic group having been essentially completely neutralised by a mercaptoamine, a thiazolidine, or a mixture thereof.

14. The process according to claim 13, wherein the ion-exchange resin is prepared before its use by washing it with distilled or deionised water until the washings exhibit a conductivity of <100 µS, then removing the water from the ion-exchange resin by drying it in a drying unit or by displacing it with anhydrous phenol, and thereafter essentially or completely neutralising it with the mercaptoamine, the thiazolidine, or the mixture thereof.

15. The process according to claim 13, further comprising removing the mineral acid and separating the ion-exchange resin from the bisphenol.

16. The process according to claim 15, wherein the separating step is carried out by filtering or centrifugating the ion-exchange resin from the bisphenol.

17. The process according to claim 15, further comprising purifying the bisphenol.

18. The process according to claim 13, wherein the mineral acid is hydrochloric acid, hydrogen chloride gas, or a mixture thereof.

19. The process according to claim 13, wherein the phenol comprises a compound selected from the group consisting of phenol, o-cresol, m-cresol, 2,6-dimethylphenol, 2-chlorophenol, 3-chlorophenol, 2,6-dichlorophenol, 2-cyclohexylphenol, diphenylphenol, o-benzylphenol, and p-benzylphenol.

20. The process according to claim 13, wherein the ketone comprises a compound selected from the group consisting of isatin, 9-fluorenone, and 2-fluoro-9-fluorenone.

21. The process according to claim 13, wherein the mercaptoamine comprises a ω-aminoalkyl mercaptan.

22. The process according to claim 1, wherein the thiazolidine comprises 2,2-dimethylthiazolidine.

23. The process according to claim 13, wherein the acidic group of the ion-exchange resin is essentially completely neutralised by the mercaptoamine or the mixture of the mercaptoamine and the thiazolidine, and in which a molar ratio of mercapto groups to the ketone is at least 1:10.

24. The process according to claim 23, wherein the molar ratio of mercapto groups to the ketone is between about 1:1 and about 10:1.

* * * * *